US010987120B2

(12) United States Patent
Heck et al.

(10) Patent No.: US 10,987,120 B2
(45) Date of Patent: Apr. 27, 2021

(54) MULTIFUNCTION SURGICAL INSTRUMENT FOR USE IN LAPAROSCOPIC SURGERY

(71) Applicants: Sandy Lawrence Heck, Los Angeles, CA (US); Eric William Conley, South Berwick, ME (US); Ricardo Alexander Gomez, Lighthouse Point, FL (US); Eric Allen Lopez, North Lauderdale, FL (US)

(72) Inventors: Sandy Lawrence Heck, Los Angeles, CA (US); Eric William Conley, South Berwick, ME (US); Ricardo Alexander Gomez, Lighthouse Point, FL (US); Eric Allen Lopez, North Lauderdale, FL (US)

(73) Assignee: NEW WAVE ENDO-SURGERY INC., Coconut Creek, FL (US)

( * ) Notice: Subject to any disclaimer, the term of this patent is extended or adjusted under 35 U.S.C. 154(b) by 417 days.

(21) Appl. No.: 15/864,243

(22) Filed: Jan. 8, 2018

(65) Prior Publication Data
US 2018/0193049 A1 Jul. 12, 2018

Related U.S. Application Data

(60) Provisional application No. 62/444,433, filed on Jan. 10, 2017, provisional application No. 62/444,434,
(Continued)

(51) Int. Cl.
*A61B 17/29* (2006.01)
*A61B 5/107* (2006.01)
(Continued)

(52) U.S. Cl.
CPC ............ *A61B 17/29* (2013.01); *A61B 5/1076* (2013.01); *A61B 5/4255* (2013.01);
(Continued)

(58) Field of Classification Search
CPC ....... A61B 17/29; A61B 90/92; A61B 5/1076; A61B 5/4255; A61B 5/6847;
(Continued)

(56) References Cited

U.S. PATENT DOCUMENTS 4,188,727 A * 2/1980 Matui .................... G01B 3/008
33/796
4,873,771 A * 10/1989 Wust ..................... G01B 3/008
33/802
(Continued)

*Primary Examiner* — Jing Rui Ou
(74) *Attorney, Agent, or Firm* — Grogan, Tuccillo & Vanderleeden, LLP

(57) ABSTRACT

The present invention is directed toward devices and methods for use in minimally invasive needlescopic procedures whereby an improved bowel grasper incorporates a means for measuring the pressure applied to a body part is translated to a visual representation. In addition, in an embodiment a rubberized bowel grasper device having a chevron style surface which is used to facilitate grabbing and manipulating body parts is provided. In another embodiment of the present invention and system a device and method for measuring distances inside the abdomen is provided. Further embodiments include bowel graspers with a combination of the above features and functions.

14 Claims, 9 Drawing Sheets

Related U.S. Application Data filed on Jan. 10, 2017, provisional application No. 62/444,435, filed on Jan. 10, 2017.

(51) Int. Cl.

| | | |
|---|---|---|
| *A61B 5/00* | (2006.01) | |
| *A61B 90/92* | (2016.01) | |
| *A61B 17/00* | (2006.01) | |
| *A61B 90/00* | (2016.01) | |
| *A61B 17/28* | (2006.01) | |

(52) U.S. Cl.
CPC ............ *A61B 5/6847* (2013.01); *A61B 90/92* (2016.02); *A61B 2017/00353* (2013.01); *A61B 2017/00438* (2013.01); *A61B 2017/00818* (2013.01); *A61B 2017/00858* (2013.01); *A61B 2017/00862* (2013.01); *A61B 2017/2825* (2013.01); *A61B 2017/2926* (2013.01); *A61B 2017/2939* (2013.01); *A61B 2090/061* (2016.02); *A61B 2090/062* (2016.02); *A61B 2090/065* (2016.02); *A61B 2090/0811* (2016.02)

(58) Field of Classification Search
CPC ........ A61B 2090/061; A61B 2090/062; A61B 2090/065; A61B 2090/0811; A61B 2017/00353; A61B 2017/00438; A61B 2017/00818; A61B 2017/00858; A61B 2017/00862; A61B 2017/2825; A61B 2017/2926; A61B 2017/2939

See application file for complete search history.

(56) References Cited

U.S. PATENT DOCUMENTS

| | | | | |
|---|---|---|---|---|
| 5,147,373 | A | | 9/1992 | Ferzli |
| 5,769,848 | A | * | 6/1998 | Wattanasirichaigoon ............ A61B 17/29 606/215 |
| 2003/0105488 | A1 | * | 6/2003 | Chu ............ A61B 17/29 606/205 |
| 2003/0171747 | A1 | * | 9/2003 | Kanehira ............ A61B 18/085 606/45 |
| 2003/0229344 | A1 | * | 12/2003 | Dycus ............ A61B 18/1445 606/51 |
| 2005/0240219 | A1 | * | 10/2005 | Kahle ............ A61B 17/122 606/207 |
| 2006/0036232 | A1 | * | 2/2006 | Primavera ............ A61B 17/0469 604/411 |
| 2013/0253275 | A1 | * | 9/2013 | Ransden ............ A61B 17/0281 600/204 |
| 2014/0330073 | A1 | * | 11/2014 | Ko ............ A61B 17/0469 600/103 |
| 2016/0270694 | A1 | * | 9/2016 | Tang ............ A61B 5/1076 |
| 2016/0270713 | A1 | * | 9/2016 | Martin ............ A61B 5/1076 |

\* cited by examiner

OPEN POSITION

CLOSED POSITION

MULTIFUNCTION SURGICAL INSTRUMENT FOR USE IN LAPAROSCOPIC SURGERY

CROSS-REFERENCE TO RELATED APPLICATIONS

This application claims the benefit of U.S. Provisional Application No. 62/444,433, filed on Jan. 10, 2017 entitled Bowel Grasper Jaws, U.S. Provisional Application No. 62/444,434 filed on Jan. 10, 2017 entitled Laparoscopic Bowel Measurement Tool, and U.S. Provisional Application No. 62/444,435, filed on Jan. 10, 2017 entitled Surgical Instrument Force Gauge, wherein are each incorporated by reference herein in their entireties.

FIELD OF THE INVENTION

The present field of invention relates to methods and devices used in Laparoscopic surgery such as for bowel grasping, bowel measuring, and visually quantifying forces applied to organs or tissue parts.

BACKGROUND OF THE INVENTION

Minimally invasive surgery has impacted the medical industry profoundly, but has also been met with numerous challenges. Since the late 1980's Laparoscopic surgery has become very popular and continued to expand. The popularity of laparoscopic surgery is mainly due to the advantages it offers to its patients. Copious methods and techniques have developed that have reduced the scaring, operating times, recovery times, loss of blood, and shorter hospital stays of patients.

Prior to starting a surgical procedure, a small incision is created allowing a trocar device to be inserted. Additional percutaneous incisions are made, between 5-15 mm, for inserting additional trocars. Trocars typically range in diameter between 5-12 mm and provide a passageway for the introduction of surgical instruments into the abdomen. An insufflator is then used to inflate the cavity thus creating the space necessary for the surgeon to perform the medical procedure and provide a viewing field.

One of the most common instruments used in laparoscopic surgery is the bowel grasper. This is a grasper instrument with jaws that are designed for effective handling of the bowel and other delicate tissues in the abdomen. Although this instrument is universally used in laparoscopic surgeries around the world, its design and features have remained unchanged since laparoscopy was introduced in the 1980's.

In U.S. Pat. No. 5,147,373 entitled "Laparoscopic Instrument" by George S. Ferzli, dated Sep. 15, 1992, [Col 1, Lines 20-23] Ferzli discloses the benefits of laparoscopic surgery, and specifically makes reference to the reduction in pain, fast recovery times, and almost invisible scars. The drawback with measuring organs inside a body cavity are that the surgeon cannot directly see what he is doing but through a monitor. The monitor size limits the field of view and magnifies the image, thereby making it difficult to ascertain distances and dimensions of body organs and tissues.

Moreover, during the surgical procedure, there are times that organs or tissues need to be measured. This is particularly the case in surgeries, such as gastric bypass procedures, where surgical technicians require that the surgeon perform different actions on the bowel and fixed distances. If distances cannot be measured accurately, many surgeries cannot be performed correctly. Unfortunately, there aren't many options to accurately measure these body organs and tissues. A rotatable wheel design has been proposed by George Ferzli in his Apr. 18, 2000, U.S. Pat. No. 6,050,960. The patent discloses how a wheel is placed in contact with an internal body part to be measured and rotation is imparted to the wheel, either by self-induced rotational components housed in the instrument which cause the wheel to be propelled along the surface with which it is in contact, or by friction-induced rotation caused by advancing a freely mounted wheel while in engaged contact with the organ surface. The wheel is rolled along a measurement path, and rotation thereof sensed and converted into data output representative of a distance traversed by the wheel. Rotational data is converted into quantitative measurements. However, rolling a wheel across a non-uniform surface is time consuming, requires the surgeon to move slowly and carefully inside a restricted area, and requires the surgeon to learn and execute a new technique, requiring additional training. Since the invention is a standalone device it requires that the user purchase an additional instrument and occupy an additional trocar.

Therefore, there is a need in the field for a laparoscopic measuring tool that can accurately measure distances inside a body cavity. There is also a need in the field for a laparoscopic measuring tool that is multifunctional, thus eliminating the need for an extra instrument or extra trocar. It would be desirable to provide laparoscopic instruments that are part of standard operating tools, incorporating a measuring device already built into it, thus making it readably available.

Nearly all laparoscopic surgeries are performed with metallic instruments. Metallic instruments are beneficial in that they are strong and can be reused, but they also have a downside. In a bowel grasper, the metallic inner surface of the jaws are constructed of hard materials, often shaped into sharp-edged teeth, and have been known to cause accidental injury or perforation to the surrounding tissues or organs during surgery. These injuries are not always noticed until after the surgery has been completed and many times lead to complications. Additionally, metallic surfaces tend to have a higher slippage rate on wet tissues, requiring the surgeon to use a tighter grip that could be damaging to tissues.

Thus, there is a need in the field for laparoscopic devices that can dramatically improve functionality by providing better gripping and softer surfaces. The gentler manipulation would allow better handling and would minimize the possibility of accidental bowel injuries during surgery, which often leads to infections and complications.

In Laparoscopic surgery, forces are often applied to body parts and organs, between the jaws of an instrument. In traditional open surgery, surgeons could feel the force of their instruments tactilely, but in laparoscopic surgery surgeons must look through a monitor to see what they are doing and often must judge how much pressure they are applying to that organ or body part by the feedback they receive visually. In modern day surgery, a problem prevails in that surgeons cannot visually quantify how much pressure they are applying to a body part. As the time involved in surgery expands and the surgeon gets tired, the amount of pressure that is being applied may not be consistent. This creates the problem of over gripping or under gripping body parts. Damaging body parts and tissues can happen when this takes place. Another time that this problem occurs is when a surgeon uses assistants to hold laparoscopic devices in place. It is currently not possible to determine if the assistant is applying to much or too little pressure to these body parts, tissues or organs, often the assistants are medical assistance or residents in training. They lack the experience to determine if the force applied is too much or too little. The solution to this would be to have a visual means of quantifying the force the assistant is applying to the body part or tissue. Therefore, there is a need in the field for a force gauge device that can translate force units into visual feedback.

Certain small measuring instruments do exist in the art for quantifying applied forces. Typically springs or coiled metals are used to measure these forces. When pressure is applied to them, depending on the configuration they either compress or expand and the difference in movement is used to determine how much pressure is being exerted.

In view of the above, however, there remains a need for a new type of surgical instrument and, in particular, a multifunction bowel grasper that combines one or more of the following three features to improve the functionality and safety of the laparoscopic bowel grasper. These features include a feature that allows the user to accurately measure distances of organs inside the body, a feature that improves the gripping surface of the instrument's jaws, and a feature that provides visual feedback regarding the pressure being applied to tissues between the instrument's jaws.

DESCRIPTION OF THE DRAWINGS

The various aspects of the present invention well be more fully understood when the following portions of the specification are read in conjunction with the accompanying drawings wherein.

SUMMARY OF THE INVENTION

Figure 1:
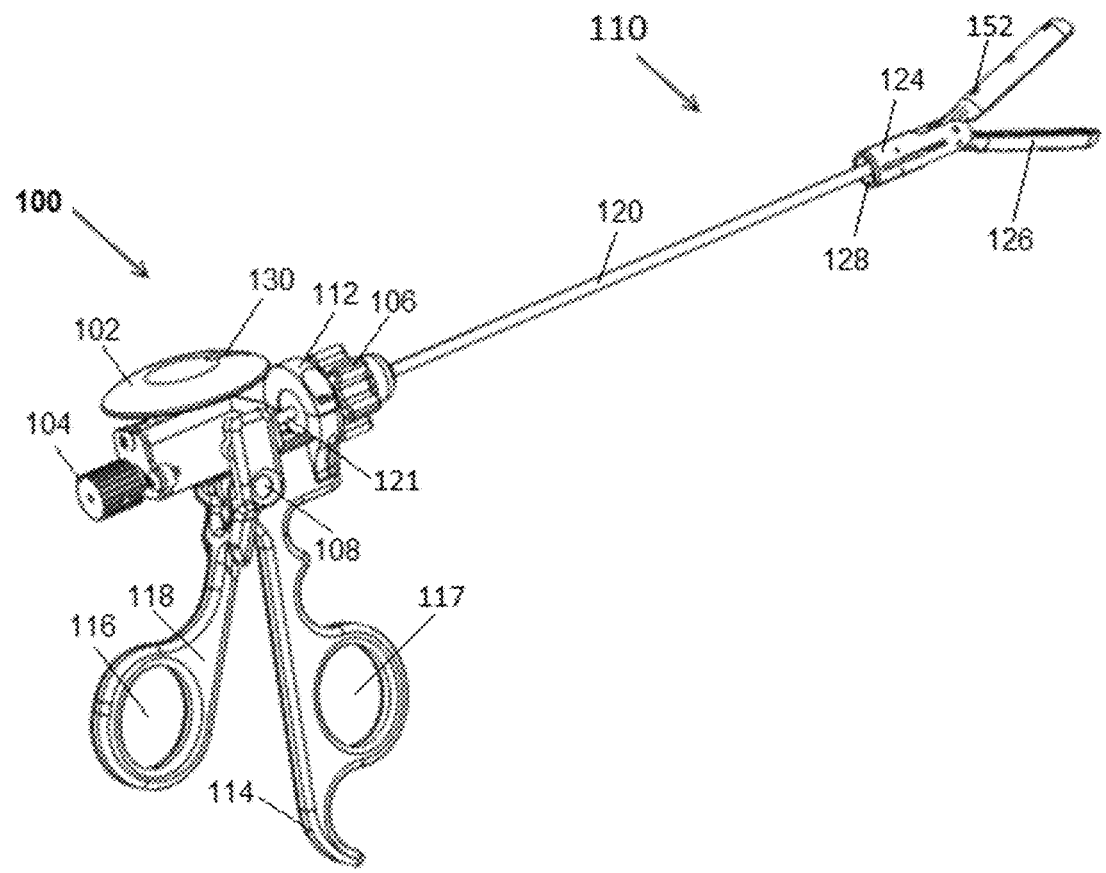
FIG. 1 is a perspective view of a surgical instrument force gauge device.

It is an object of the preset invention to provide a surgical instrument that overcomes the deficiencies of the known art and the problems that remain unsolved by converting a tactical means of measuring pressure to a body part in the abdomen to visual measurable indicator device.

It is another object of the present invention to provide a surgical instrument that includes a means of holding body parts through the use of a rubberized instrument head grasper and a means of measuring length inside the abdomen of a patient.

The present invention is directed toward devices and methods for use in minimally invasive needlescopic procedures whereby an improved bowel grasper incorporates a means for measuring the pressure applied to a body part is translated to a visual representation. In addition, in an embodiment a rubberized bowel grasper device having a chevron style surface which is used to facilitate grabbing and manipulating body parts is provided. In another embodiment of the present invention and system a device and method for measuring distances inside the abdomen is provided. Further embodiments include bowel graspers with a combination of the above features and functions.

A person skilled in the art will appreciate that while the methods and devices described in this application are not limited to but may be used in connection with laparoscopic surgery, may also be employed in needlescopic surgery in which one or more surgical instruments are inserted into the abdomen of a patient with or without the use of a trocar. Several goals of this invention are the reduction of large incisions associated with traditional surgery. Quicker recovery periods for the patient, and a lower likely hood of infections in the affected area.

It will also be appreciated by a person skilled in the art that these specialized tools significantly improve the determination of quantitative measurements. Those being applied pressure, and distances measured inside the abdominal cavity.

DETAILED DESCRIPTION OF THE PREFERRED EMBODIMENTS

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

With reference to FIG. 1, a surgical instrument (110) according to an embodiment of the present invention includes a Bowel Measurement Tool (100) having a Dial Plate (102), with an Inspection Window (130), used for visually inspecting the amount of squeezing pressure being applied to a surface by the Bowel Grasper (126). A color-coded system is used including, not limited to but, the colors red and green for visually indicating proper pressure amounts. This visual system for applying safe gripping pressure may be adjusted based on the area of concern. An Elongated Shaft (120), is connected to the Instrument Head Assembly (124) at the Shaft Attachment Point (128).

The handle area consists of a Stationary Finger Rest (114), having an Inner Stationary Finger Holder (117) both used to insert the operators fingers not shown, for controlling the pressure applied at the Bowel Grasper (126). A Movable Handle Neck (118), having an Outer Movable Finger Holder (116) are in the same movable body. The Outer Movable Finger Holder (116) pivots about the Pivoting Device (108), used to manually apply pressure by hand through the shaft to the Bowel Grasper (126). The Inner Shaft Locking Knob (104) is attached to the Bowel Grasper (126) near the Shaft Attachment point (128), the main purpose of which is to manually attach and release control of the Bowel Grasper (126). The Outer Shaft Locking Knob (106) is the means used to attach the Instrument Head Assembly (124) to the Elongated Shaft (120) at the Shaft Attachment Point (128). The Inner Shaft Locking Knob (104) and the Outer Shaft Locking Knob (106) are designed to rotate in opposite directions when being secured. This provides an additional safety feature for holding the Bowel Grasper (126) secured.

Figure 2A:
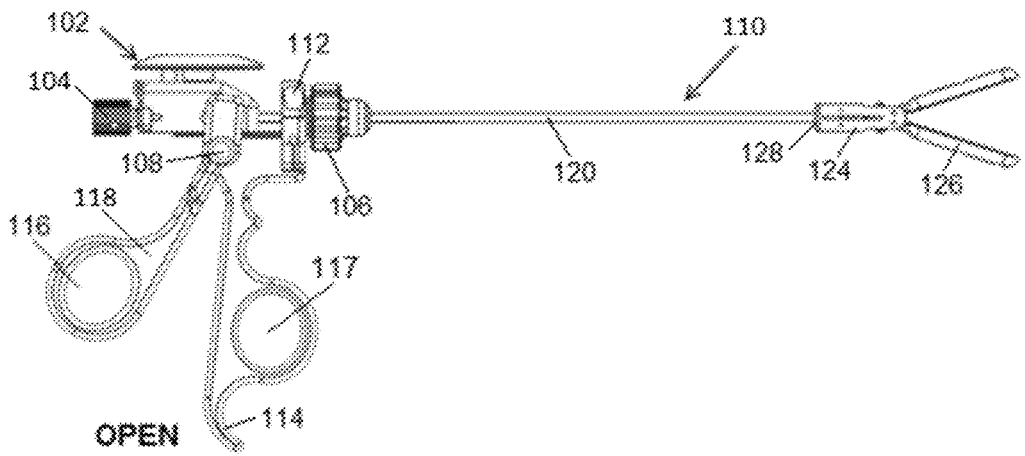
FIG. 2A is a side perspective view of a surgical instrument force gauge device in its open position.
Figure 2B:
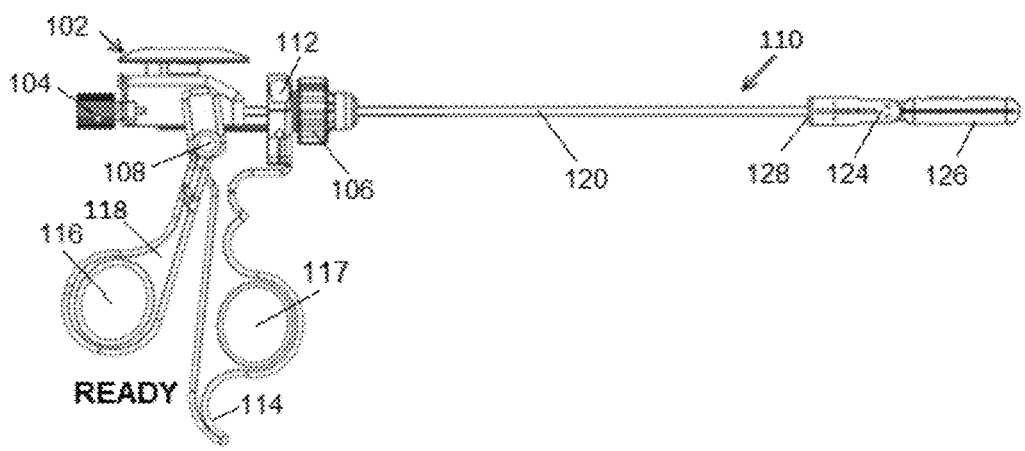
FIG. 2B is a side perspective view of a surgical instrument force gauge Device in its ready to measure force position.
Figure 2C:
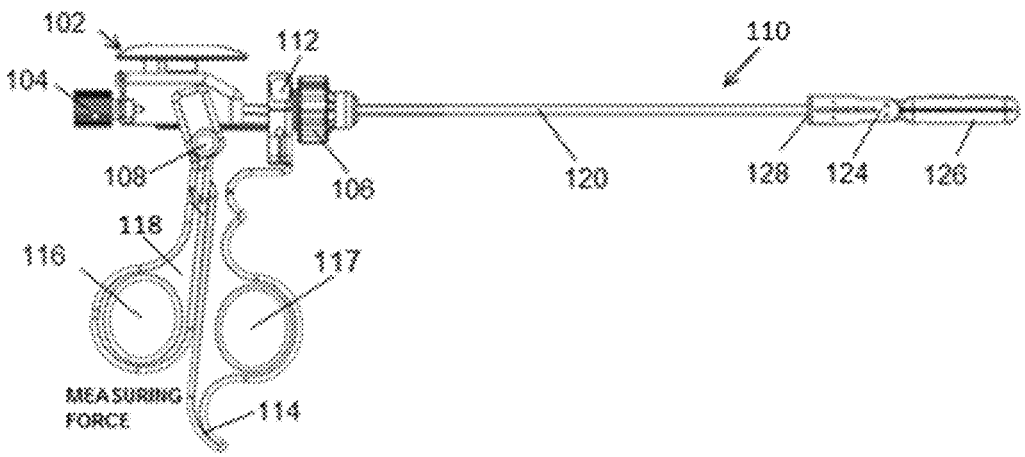
FIG. 2C is a side perspective view of a surgical instrument force gauge device in its measuring position.

With respect to FIGS. 2A-2C, the three positions of the Surgical Instrument Force Gauge (100) are illustrated. In position 2A the open finger holders correspond to an open Bowel Grasper (126). This is typically the pre-engaged position. In the pre-engaged position, the user manipulates the device to the desired location in the abdomen. In FIG. 2B the Instrument Force Gauge (100) is in the ready position for measuring force. A more detailed explanation will be found under explanation of FIG. 4A-4B. In FIG. 2C the Surgical Instrument Force gauge (100) is seen in the full measuring position.

Figure 3A:
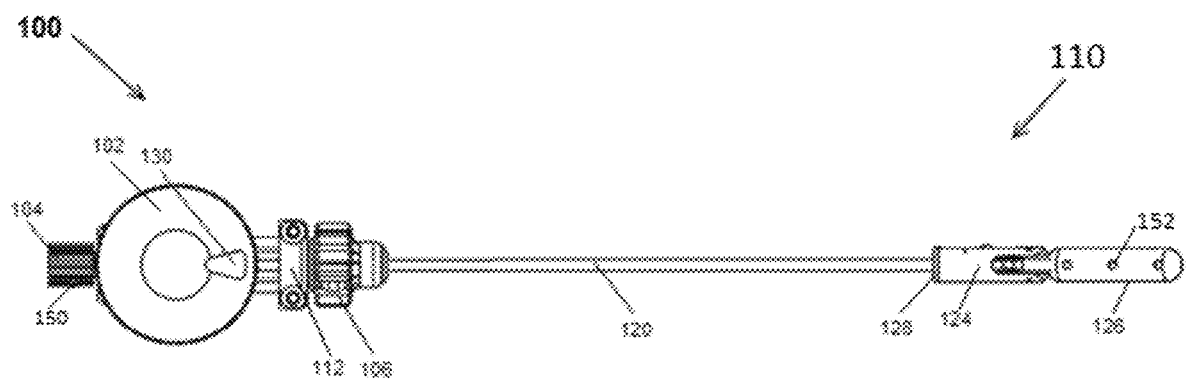
FIG. 3A is a top perspective view of a surgical instrument force gauge device illustrating the inspection window.

With respect to FIG. 3A a top view of the Surgical Instrument Force Gauge (100) is illustrated, showing how the Inspection Window (130) is easily visible to the user. When no pressure is being applied, no color coding is displayed in the window. When pressure begins to be applied the Visual Indicator Device (138) moves displaying color codes letting the user visually see if they are applying a safe amount of pressure. It should be noted that the application of pressure is not limited to but includes a color coding scheme. It may also incorporate but is not limited to numeral values of pressure allowing the user to determine what is an appropriate value. The configuration of the Inner Shaft Locking Knob (104) and Outer Shaft Locking Knob (106) make them easily accessible and controlled by the user when attaching the Bowel Grasper (126).

Figure 3B:
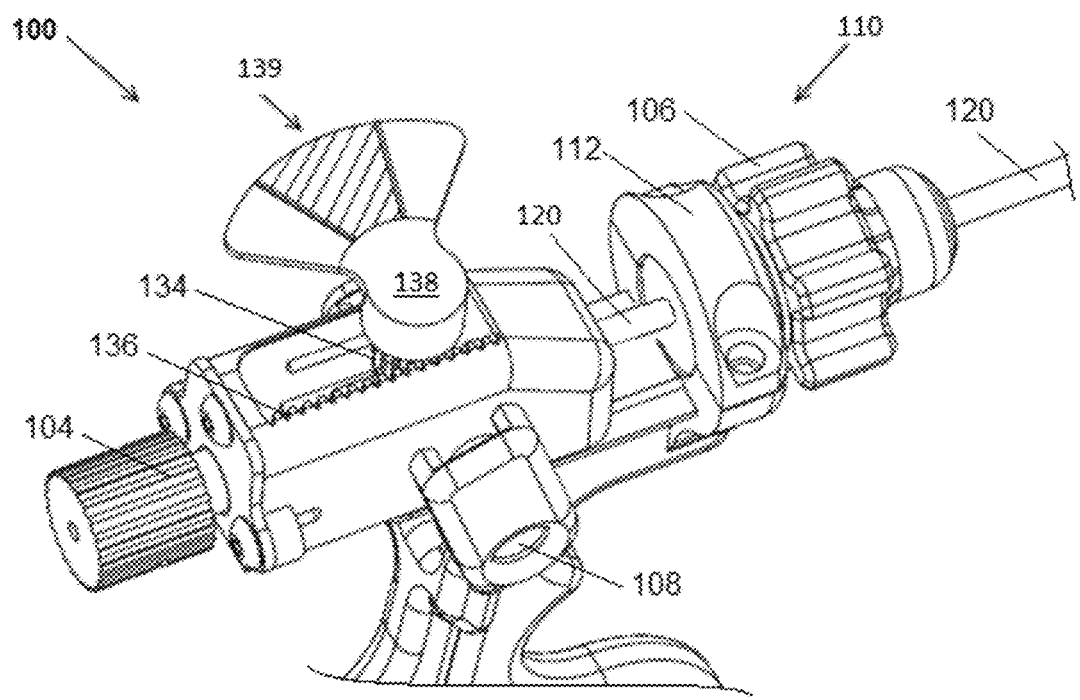
FIG. 3B is a sectional view of a surgical instrument force gauge device illustrating the visual indicator device.

With respect with FIG. 3B a perspective view of the Surgical Instrument Force gauge (100) is illustrated without the Dial Plate (102). A Rack Assembly (136) is used to guide a Dial Gear (134) as it spins and causes the Visual Indicator Device (138) to rotate clockwise and causes the color-coded section VID (139) to also rotate. Elongated Shaft (120) passes through the Outer Shaft Locking Knob (106) and the Outer Guide Shaft Controller (112) to its proximal end where it is attached to the Inner Shaft Locking Knob (104). Shaft Locking Knob (106) is designed in a gear shape allowing easier grasping of the fingers. Pivoting Device (108) permits the transfer of finger movement to linear movement of the Elongated Shaft (102) which in turn controls the opening and closing of the Bowel Grasper (126).

Figure 4A:
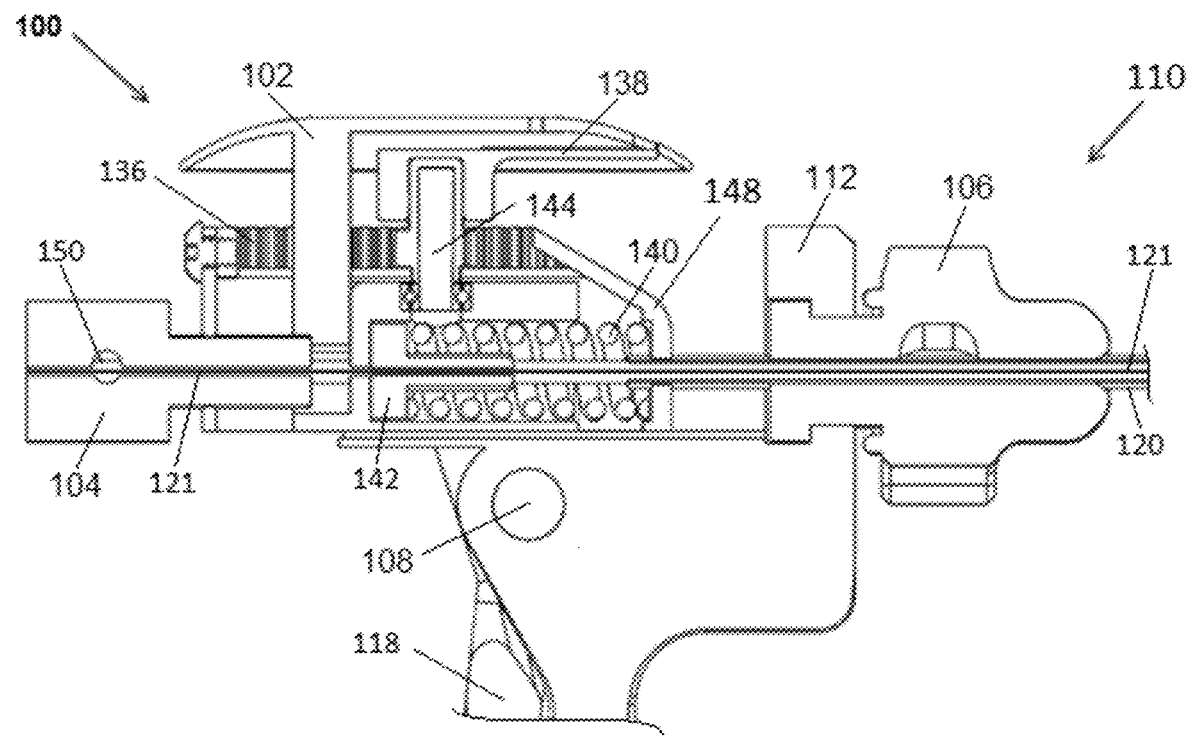
FIG. 4A is side sectional view of the handle section of a surgical instrument force gauge device.

With respect to FIG. 4A a sectional view of the Surgical Instrument Force Gauge (100) is illustrated, depicting how the Elongated Inner Shaft (121) passes through the device and connects to the Inner Shaft Locking Knob (104). The Inner Shaft Locking Knob (104) holds in place the Elongated Inner Shaft (121) by placement of a Locking Screw (150). When Bowel Grasper (126) is in the engaged position (FIG. 5B Locked Position), the Inner Shaft (121) is held stationary throughout. Continued movement of the Movable Handle Neck (118) causes the Housing Body (148) to apply pressure to Spring Assembly (140) which is held in place by the Spring Retainer Stop (142) causing a rotational action of the VID Shaft (144) along the Rack Assembly (136). This action which results in the Dial Gear (134) to rotate clockwise.

Figure 4B:
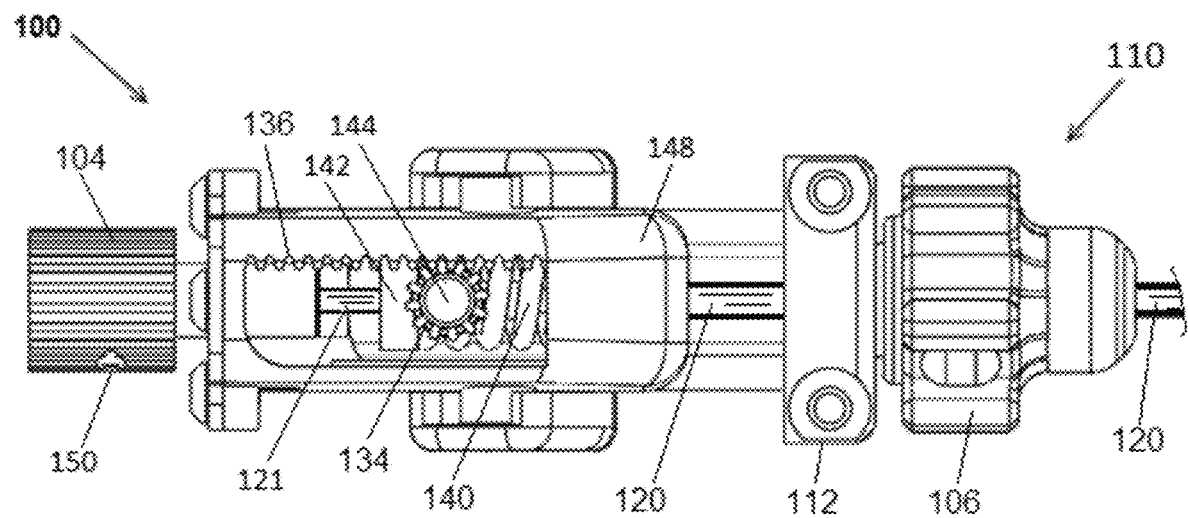
FIG. 4B is a top sectional view of a surgical instrument force gauge device.

With respect to FIG. 4B a top view of the Surgical Instrument Force Gauge (100) without the Dial Plate (102) or Visual Indicator Device (138) is depicted, clearly showing how the Dial Gear (134) rotates about the Rack Assembly (136).

Figure 5A:
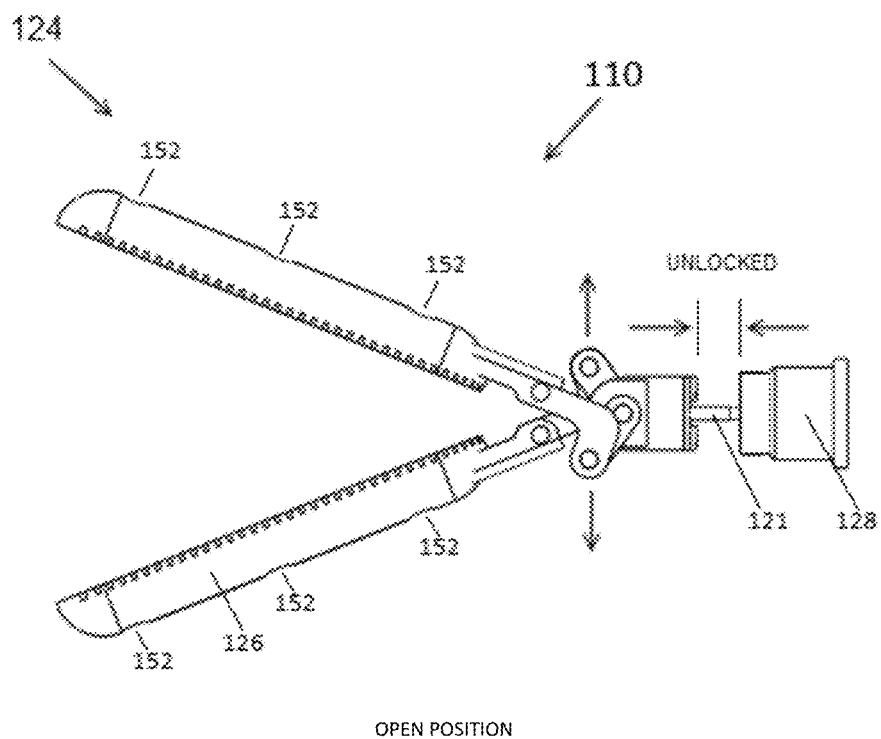
FIG. 5A is a side perspective view of the instrument head assembly in the unlocked position.
Figure 5B:
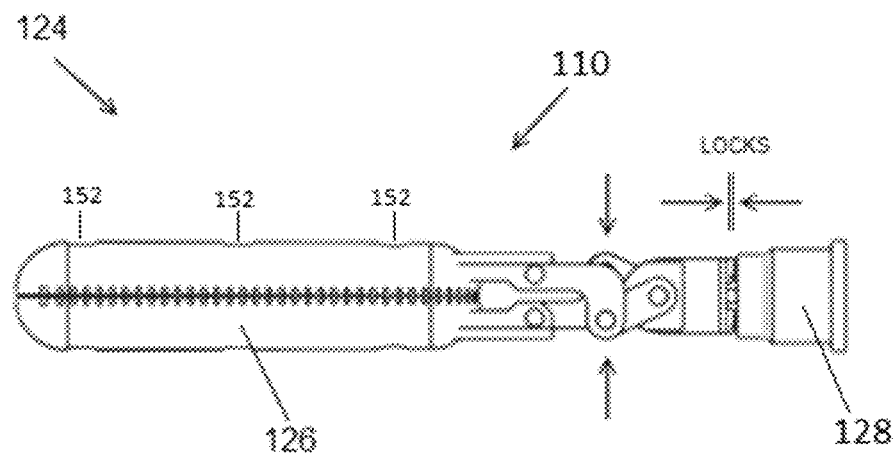
FIG. 5B is a side perspective view of the instrument head assembly in the locked position.

With respect to FIG. 5A the Bowel Grasper (126) is illustrated in the open position prior to engaging a surface. When the Bowel Grasper (126) is in the open unlocked position the distal end of Elongated Inner Shaft (121) is exposed. When the Bowel Grasper (100) reaches the ready position as illustrated in FIG. 5B the Elongated Inner Shaft (121) is no longer visible and provides a physical resistance to the Spring Retainer Stop (142) of FIG. 4A causing the Spring Retainer Stop (142) to begin compressing the Spring Device (140). As the Spring Device is compressed (140) the VID Shaft (144) spins the Dial Gear (134) along the Rack Assembly (136) causing the Visual Indicator Device (138) to rotate.

Figure 6:
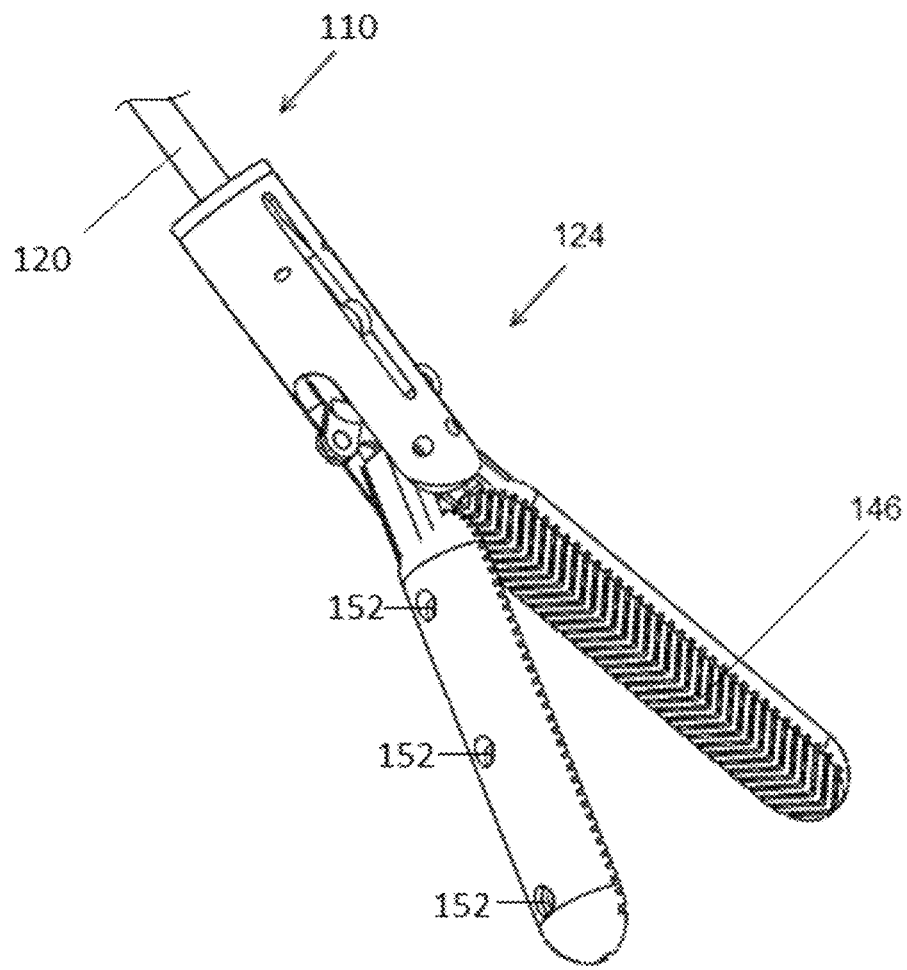
FIG. 6 is a perspective view of an alternative instrument head assembly having rubberized graspers.

With respect to FIG. 6 a specialized Instrument Head Assembly (124) having a Rubberized Grasper (146) may be used in place of the original Bowel Grasper (126) of FIG. 1. The rubberized inner surface of the Bowel Grasper (126) may also incorporate a specialized gripping surface. Several Rubberized Surface Securing Holes (152) provide a means of locking in place the rubberized surface to the metalized grasper surface.

Figure 7:
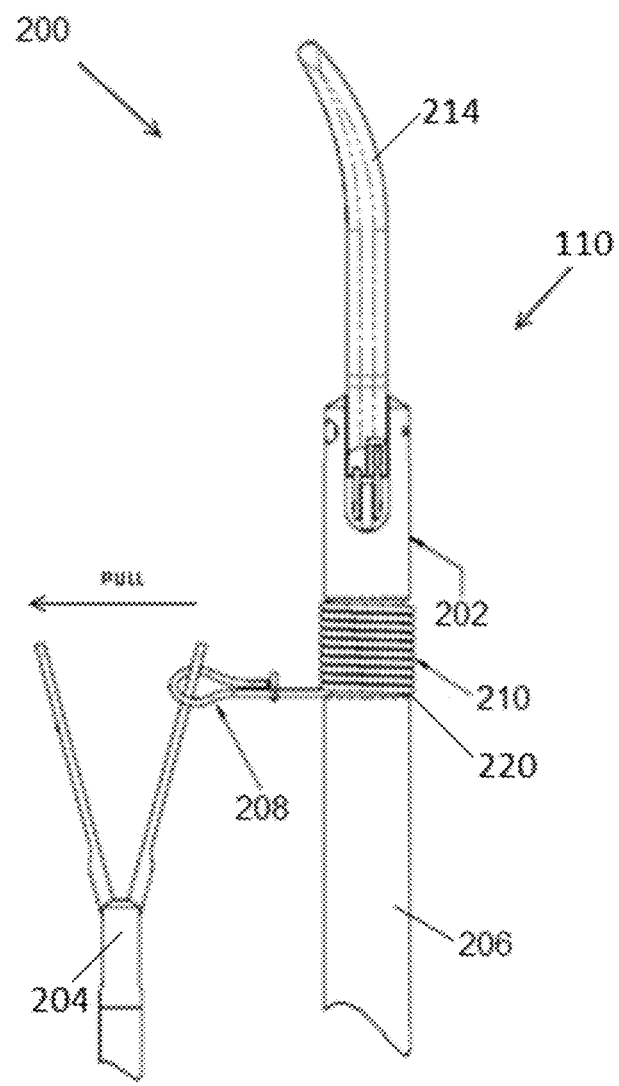
FIG. 7 is a perspective view of a bowel measurement tool.
Figure 8:
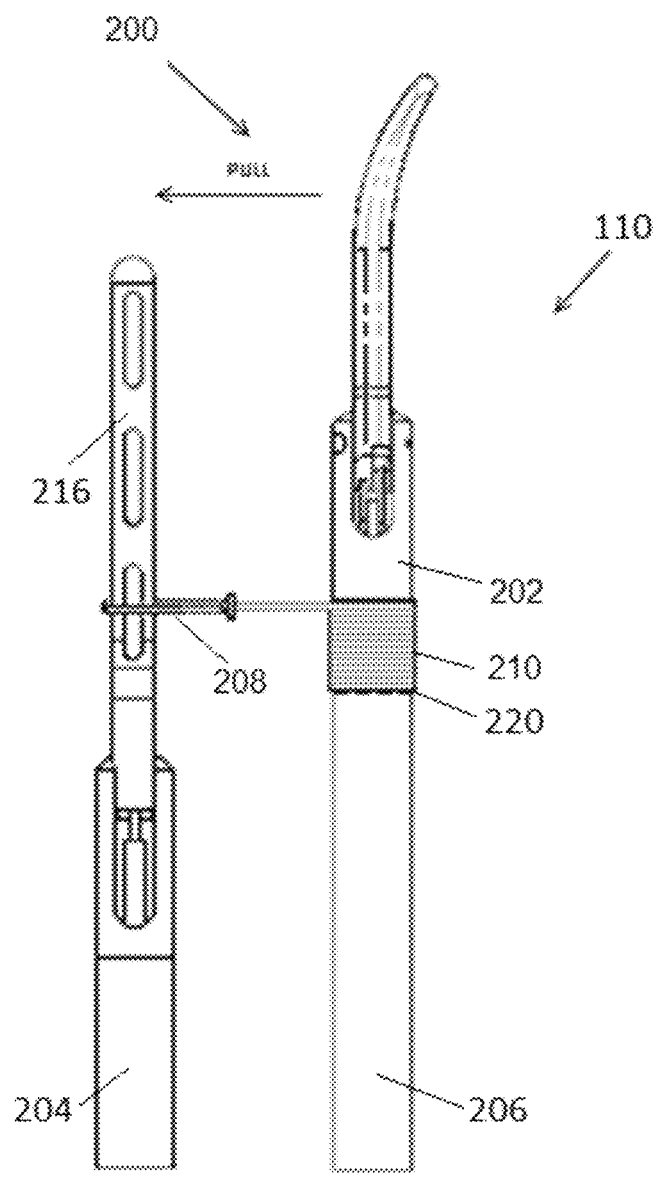
FIG. 8 is a perspective view of the bowel measurement tool in its pre-deployed position.

With respect to FIGS. 7 and 8, a Bowel Measurement Tool (200) is illustrated having a Rotating Shaft (206), or sub-segment of shaft, that spins independently around the Bowel Head Shaft (202) when the Measuring String (210) is extended. Extension of the Measuring String (210) is accomplished by pulling the Measuring String Loop (208) by a Secondary Grabbing Device (216). This feature permits the Bowel Grasper (214) to remain stationary when engaged while allowing the Measuring String Loop (208) to extend to the desired measuring length.

Figure 9:
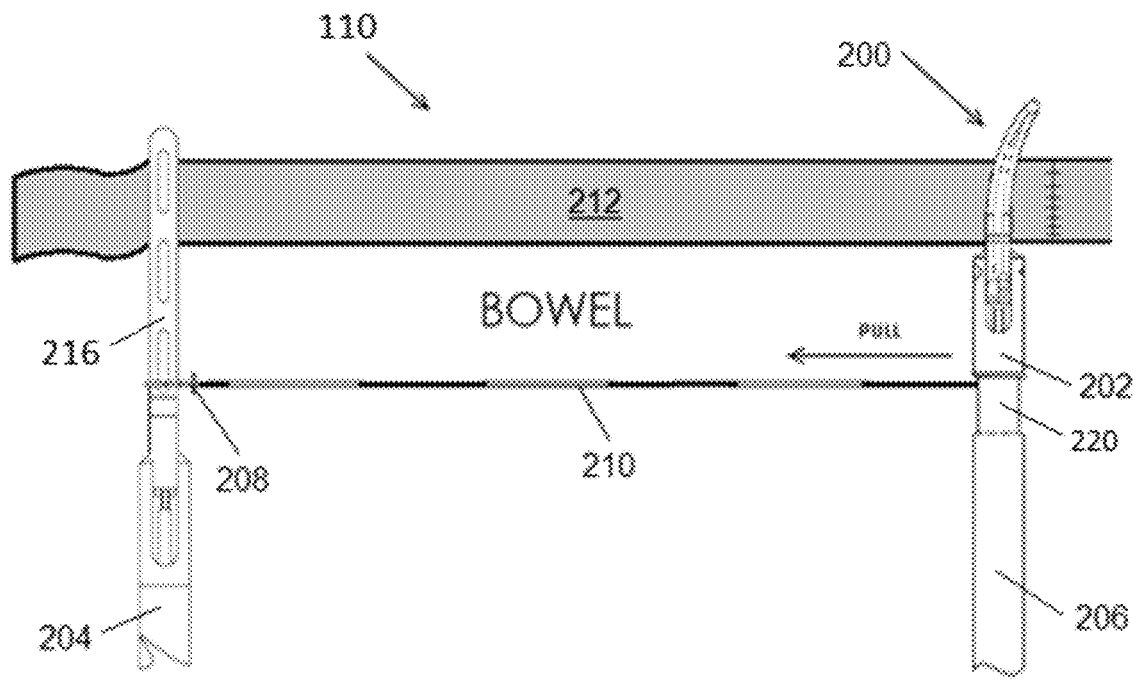
FIG. 9 is a perspective view of the bowel measurement tool in its fully deployed position.

With respect to FIG. 9 Bowel (212) is measured by the Bowl Measuring String (210). The Bowl Measuring String (210) may include but is not limited to a color-coded scheme corresponding to predetermined distance increments. These predetermined visual indicators allow the surgeon to quickly determine the length of area being measured. The Secondary Grabbing Device (216) is inserted inside the String Loop (208) allowing the surgeon to place at a predetermined distance. In summary the surgical instrument (110) for use in laparoscopic surgery comprises a laparoscopic length measuring tool, a tissue grasper having rubberized jaws and a gauge which provides visual indication of the pressure being applied by the tissue grasper upon tissue clamped between the rubberized jaws.

The present invention therefor provides a surgical instrument (110) that includes a gauge which comprises an element which, when the jaws are in a maximally closed but gapped and locked position with tissue grasped therebetween, the gauge (138) is activated to visually indicate whether the pressure applied is acceptable or excessive, allowing for adjustment of the pressure. The surgical instrument (110) may further include an inner grasper movement controller shaft and an outer shaft for securing the grasper in position wherein the pressure readings provided by the gauge are translated to linear movements of the inner shaft (121) relative to the outer shaft (120). In an embodiment, the pressure produced by an outer movable finger holder (116) of the surgical instrument (110), which engages and controls a housing of the instrument in a manner wherein a spring (140) within the housing (148) seated about the outer shaft (120) and against a spring retainer stop (142), is measured by the gauge (138). In an embodiment, the surgical instrument (110) has a rotating shaft (144) that mounts a gear (134) which moves along a rack assembly (136) of the housing (148) which causes the rotation of the shaft (144) which in turn causes a rotational movement of the visual indicator (138) to apprise of a particular predetermined pressure associated with the rotational position of the shaft (144).

In an embodiment, the surgical instrument (110) may also include a bowel measurement tool which incorporates a measuring string (210) which is wound around a shaft of the tool and incorporates a proximal end loop (208) which is engaged to pull the string (210) proximally outward. The surgical instrument (110), wherein the measurement tool (200) remains stationary while the bowel measuring string (210) is being pulled to a desired location and the string (210) spins within a helical groove or recess (220) around the measuring tool shaft (206) as the string is pulled to a desired length. In an embodiment, the string (210) of the bowel measuring tool (200) includes a color-coded measuring scheme.

In an embodiment, the grasper is constructed of rubberized material for superior grasping. In an embodiment, the tissue grasper is constructed of rubberized material having a chevron surface pattern.

In an embodiment, the surgical instrument (110) is suited for use in intestinal and gallbladder laparoscopic procedures.

While the invention has been described with reference to the preferred embodiments, it will be understood by those skilled in the art that various obvious changes may be made, and equivalents may be substituted for elements thereof, without departing from the essential scope of the present invention. Therefore, it is intended that the invention not be limited to the particular embodiments disclosed, but that the invention includes all embodiments falling within the scope of the appended claims.

What is claimed is:

1. A multifunction surgical instrument comprising:
a laparoscopic tissue grasper having jaws having rubberized gripping elements;
a laparoscopic length measuring tool having a measuring string wound about the multifunction surgical instrument at a point adjacent to the jaws; and
a gauge which provides visual indication of a pressure being applied by the tissue grasper upon tissue clamped by the jaws.

2. The multifunction surgical instrument claim 1, wherein:
the gauge includes an element which, when the jaws are in a maximally closed but spaced and locked position with tissue grasped therebetween, the gauge is activated to visually indicate whether pressure applied to the tissue is within a predetermined acceptable range, allowing for adjustment of the pressure.

3. The multifunction surgical instrument claim 1, further comprising:
an inner grasper movement controller shaft and an outer shaft for securing the tissue grasper in position, wherein pressure readings provided by the gauge are translated to linear movements of the inner grasper movement controller shaft relative to the outer shaft.

4. The multifunction surgical instrument claim 3, wherein:
pressure produced by an outer movable finger holder of the surgical instrument, which engages and controls a housing of the surgical instrument in a manner wherein a spring within the housing seated about the outer shaft and against a spring retainer stop, is measured by the gauge.

5. The multifunction surgical instrument claim 4, wherein:
the spring retainer stop causes a shaft of the visual indicator to rotate to a position indicative of a particular pressure being applied.

6. The multifunction surgical instrument claim 5, wherein:
the rotating shaft of the visual indicator mounts a gear which moves along a rack assembly of the housing which causes the rotation of the shaft of the visual indicator which in turn causes a rotational movement of the visual indicator to apprise of a particular predetermined pressure associated with the rotational position of the shaft of the visual indicator.

7. The multifunction surgical instrument claim 1, wherein:
the laparoscopic length measuring tool is a bowel measurement tool having the measuring string which is wound around a shaft of the tool and incorporates a proximal end loop which is engaged to pull the string proximally outward.

8. The multifunction surgical instrument of claim 7, wherein:
the bowel measurement tool is operable such that the measurement tool remains stationary while the string is being pulled to a desired location and the string spins within a helical groove or recess around the shaft as the string is pulled to a desired length position.

9. The multifunction surgical instrument of claim 8, wherein:
the string of the bowel measurement tool includes a color-coded measuring scheme.

10. The multifunction surgical instrument of claim 1, wherein:
the rubberized gripping elements of the tissue grasper have a rubberized material forming a grasping surface of the jaws.

11. The multifunction surgical instrument of claim 10, wherein:
the jaws include a plurality of openings along a length of the jaws for securing the rubberized gripping elements to the jaws.

12. The multifunction surgical instrument of claim 1, wherein:
the rubberized gripping elements have a chevron surface pattern on a gripping surface thereof.

13. The multifunction surgical instrument of claim 1, wherein:
the surgical instrument is configured for use in intestinal and gallbladder laparoscopic procedures.

14. A multifunction surgical instrument for use in laparoscopic surgery, comprising:
a tissue grasper having rubberized jaws;

a laparoscopic length measuring tool having a measuring string wound about the multifunction surgical instrument at a point adjacent to the rubberized jaws; and a gauge which provides a visual indication of pressure being applied by the tissue grasper to tissue clamped between the rubberized jaws.

* * * * *